United States Patent [19]
Montminy et al.

[11] Patent Number: 5,741,673
[45] Date of Patent: Apr. 21, 1998

[54] NUCLEIC ACID ENCODING A NOVEL HOMEOBOX FACTOR WHICH STIMULATES INSULIN EXPRESSION IN PANCREATIC ISLET CELLS

[75] Inventors: Marc R. Montminy, Encinitas; James N. Leonard, San Diego, both of Calif.

[73] Assignee: Research Development Foundation, Carson City, Nev.

[21] Appl. No.: 583,672

[22] Filed: Jan. 5, 1996

Related U.S. Application Data

[63] Continuation of Ser. No. 106,936, Aug. 16, 1993, abandoned.

[51] Int. Cl.$^6$ .................................................. C12N 15/12
[52] U.S. Cl. ............... 435/69.1; 435/252.3; 435/254.11; 435/325; 435/320.1; 536/23.5; 536/24.31
[58] Field of Search ..................... 536/23.5, 24.31; 435/69.1, 325, 320.1, 252.3, 254.11

[56] References Cited

PUBLICATIONS

Karlsson, Nature, vol. 344, p. 879, 1990.
Singh et al., PNAS, vol. 88, p. 10706, 1991.
Sambrook et al., Molecular Cloning, A Lab. Manual, vol. 3, chp. 16, 1989, Cold Spring Harbor Lab. Press.
Gehring, "The homeobox in perspective," TIBS 17:277–280 (1992).
Leonard et al., "The LIM family transcription factor Isl–1 requires cAMP response element binding protein to promote somatostatin expression in pancreatic isle cells," Proc. Natl. Acad. Sci. USA 89:6247–6251 (1992).
Ohlsson et l., "Novel Insulin Promoter—and Enhancer–Binding Proteins That Discriminate between Pancreatic α— and β—Cells," Mol Endo. 5:897–904 (1991).
Ohlsson and Edlund, "Sequence–Specific Interactions of Nuclear Factors with the Insulin Gene Enhancer," Cell 45:35–44 (1986).
Vallejo et al., "Somatostatin Gene Transcription Regulated by a Bipartite Pancreatic Islet D–cell–specific Enhancer Coupled Synergetically to a cAmp Response Element," The Journal of Biological Chemistry 267:12868–12875 (1992).
Wedeen et al., "Evidence for a new family of evolutionarily conserved homeobox genes," Nucleic Acids Research 18:1908 (1990).
Wright et al., "XlHbox 8: a novel Xenopus homeo protein restricted to a narrow band of endoderm," Development 105:787–794 (1989).

Primary Examiner—John Ulm
Assistant Examiner—Sally P. Teng
Attorney, Agent, or Firm—Benjamin Aaron Adler

[57] ABSTRACT

In accordance with the present invention, there are provided novel homeobox-type pancreatic islet transcription factor proteins useful to bind to tissue-specific elements (TSEs) within a pancreatic islet hormone gene promoter and modulate hormone gene expression both in vivo and in vitro. Nucleic acid sequences encoding such transcription factor proteins and assays employing same are also disclosed. The invention transcription factor proteins can be employed in a variety of ways, for example, to modulate RNA transcription, for production of antibodies thereto, in therapeutic compositions and methods employing such proteins and/or antibodies.

9 Claims, No Drawings

NUCLEIC ACID ENCODING A NOVEL HOMEOBOX FACTOR WHICH STIMULATES INSULIN EXPRESSION IN PANCREATIC ISLET CELLS

This is a continuation of application Ser. No. 08/106,936, filed on Aug. 16, 1993, now abandoned.

This invention was made with Government support under Grant Number GM37828, awarded by the National Institutes of Health. The Government has certain rights in this invention.

FIELD OF THE INVENTION

The present invention relates to nucleic acids and receptor proteins encoded thereby. Invention nucleic acids encode novel tissue-specific pancreatic hormone transcription factor proteins. The invention also relates to methods for making such transcription factors and for using the transcription factor proteins to modulate hormone gene expression from pancreatic islet hormone gene promoters both in vivo and in vitro.

BACKGROUND OF THE INVENTION

The endocrine pancreas consists primarily of islet cells that synthesize and secrete the peptide hormones glucagon (A-cells), insulin (B-cells), somatostatin (D-cells), and pancreatic polypeptide (F-cells). Embryologically derived from the small intestine, these pancreatic islet cells may retain regulatory pathways which originated in the gut to direct expression of the same peptide hormone genes. The fetal endocrine pancreas is populated by pluripotent cells which co-express somatostatin, insulin and glucagon. As these stem cells mature, their endocrine hormone repertoire becomes restricted to expression from a single gene suggesting that, whereas common transcription factors may initially regulate all three genes, distinct nuclear transcription factor proteins must subsequently specify tissue-specific peptide production in individual mature islet cell types.

Relative to the expression of glucagon and insulin, the onset of expression of somatostatin is delayed. In the mouse, expression of the somatostatin gene occurs at day 17 of embryonic development in cells that coexpress the insulin gene, which is subsequently repressed in mature somatostatin-producing D-cells. In a different subset of cells that still coexpress both the insulin and somatostatin genes, the pancreatic polypeptide gene is activated, and subsequently both the insulin and somatostatin genes are repressed. This pattern of developmental regulation suggests that the expression of the insulin and somatostatin genes are under both positive and negative control mechanisms.

It has also been observed that expression of the somatostatin gene in the rat pancreatic islet cell line Tu-6 requires a tissue-specific promoter element (TSE) which operates in concert with the cAMP response element (CRE) to provide high-level constitutive activity. TSE-like sequences are reiterated 3 times over a 500 bp region of the somatostatin promoter, with the promoter proximal TSEs, located at $-300$ and $-100$, being most active. The somatostatin TSEs contain a canonical TAAT motif which is generally recognized by homeobox-type proteins. The homeobox factor ISL-1, for example, can bind to the TSE and regulate somatostatin expression in the rat insulinoma cell line RIN 5AH. However, ISL-1 appears to comprise only a negligible fraction of TSE binding activity in extracts of somatostatin-producing TU-6 cells. In addition to pancreatic islets, the somatostatin gene is expressed in neurons, C-cells of the thyroid gland, and D-cells of the digestive tract.

Although a number of homeobox-type factors have been proposed as key regulators of individual genes in the pancreas, their structure, cellular distribution and relative abundance remain substantially uncharacterized.

An important function of pancreatic hormones is to control vascular fluid levels of glucose. Glucagon is synthesized by the A cells of the islets of Langerhans and released in response to low blood glucose levels. Glucagon primarily affects liver cells, where it induces adenylate cyclase and the cAMP cascade, causing a degradation of glycogen and an increase in blood glucose. Glucose availability for metabolism is regulated during periods of abundance (following a meal) or scarcity (following fasting) by the adjustment of insulin and glucagon concentrations in the circulation.

When, after a meal, blood glucose rises above its normal level of 80 to 90 mg per 100 ml, insulin is released into the blood from secretory vesicles in the B cells in the islets of Langerhans of the pancreas. The islet cells themselves respond to the rise in level of glucose or amino acid levels by releasing insulin into the blood, which transports it throughout the body. By binding to cell surface receptors, insulin causes removal of glucose from the blood and its storage as glycogen. If glucose falls below about 80 mg per 100 ml, then the A cells of the islets begin secreting glucagon. The glucagon binds to a glucagon receptor on liver cells, activating adenylate cyclase and the cAMP cascade (a reaction similar to that of epinephrine). The result is the degradation of glycogen and the release of glucose into the circulation.

The disease diabetes is caused by insufficient insulin action in the body and can result from a variety of defects involved in the regulation of insulin levels. For example, abnormal function or regulation of insulin receptors has been demonstrated in some persons with diabetes. The disease can also be caused by the absence of normal insulin synthesis due to the production of a structurally abnormal insulin, or a defect in the conversion of proinsulin to insulin. Childhood, or early onset, diabetes is caused by deficient or abnormal insulin synthesis by the B cells of the pancreatic islets. In most of these circumstances injections of insulin can overcome the problem. Thus, methods to increase the levels of insulin within a diabetic patient are desirable to treat patients with particular forms of diabetes.

BRIEF DESCRIPTION OF THE INVENTION

In accordance with the present invention, there are provided novel homeobox-type transcription factor proteins. Invention proteins are derived from pancreatic islet cells and are useful for modulation of hormone gene expression both in vivo and in vitro. In addition, these proteins, or fragments thereof, are useful as immunogens for producing anti-transcription factor antibodies.

Isolated nucleic acid molecules, and recombinant cells containing such molecules, which encode the above-described pancreatic islet transcription factor proteins, are also provided. The nucleic acid molecules described herein can be incorporated into a variety of expression systems known to those of skill in the art. In addition, the nucleic acid molecules of the present invention are useful as probes for assaying for the presence and/or amount of a pancreatic islet transcription factor gene or mRNA transcript in a given sample. The nucleic acid molecules described herein, and fragments thereof, are also useful as primers and/or templates in a PCR reaction for amplifying genes encoding pancreatic islet transcription factors.

Antibodies that are immunoreactive with invention pancreatic islet hormone transcription factor proteins are also provided. These antibodies are useful in diagnostic assays to determine levels of pancreatic islet transcription factor proteins present in a given sample, e.g., tissue samples, Western blots, and the like. The antibodies can also be used to purify pancreatic islet transcription factor proteins.

Methods to regulate transcription from a promoter controlling an endocrine pancreatic hormone gene are provided. Also provided are methods for modulating the level of insulin in a mammal and for treating diabetes in a mammal in the presence of glucose.

DETAILED DESCRIPTION OF THE INVENTION

In accordance with the present invention, there are provided isolated mammalian homeobox-type transcription factor proteins. The phrase "homeobox-type transcription factor" or "transcription factor protein" refers to a protein that is able to bind to native promoter regions of pancreatic islet hormone genes and modulate mRNA transcription.

Use of the terms "isolated" and/or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant DNAs, RNAs, polypeptides and proteins of the invention are useful in ways described herein that the DNAs, RNAs, polypeptides or proteins as they naturally occur are not.

As used herein, "mammalian" refers to the variety of species from which the invention transcription factor protein is derived, e.g., human, rat, mouse, rabbit, monkey, baboon, chicken, bovine, porcine, ovine, canine, feline, and the like.

As used herein, "homeobox" refers to a domain of about 60–65 amino acids within the invention transcription factor that binds to specified nucleotide sequences within a given gene promoter region. See, Gehring, W., *TIBS*, 17:277–280, (August/1992), for a general discussion of homeobox domains. The homeobox domain of the invention protein preferably binds to either one or both of the "tissue-specific promoter element(s)" (TSE) set forth in SEQ ID NOs 3 and 4 corresponding to TSE-I and TSE-II, respectively. An exemplary homeobox domain has substantially the same amino acid sequence as amino acids 146–205 of SEQ ID NO:2.

Within the homeobox domain, there is an α-helix that participates in DNA-binding specificity referred to as the "recognition helix". The recognition helix typically occurs at approximately amino acids 42–52 of an invention protein homeobox domain (e.g., amino acids 187–197 of SEQ ID NO:2). In a preferred embodiment, the invention transcription factor protein contains a histidine amino acid residue at position 44 of the homeobox domain, e.g., amino acid position 189 of SEQ ID NO:2.

The phrase "binds to a promoter", or grammatical variations thereof, refers to the well-known association of DNA-binding transcription factors (e.g., cro repressor, lambda repressor, and the like) with particular regions of nucleic acids so as to regulate RNA transcription (see, e.g., Freifelder, D., *Molecular Biology*, 188–194 (2d ed. 1987). The invention transcription factor binds to at least one nucleotide tissue-specific response element within a promoter region selected from a mammalian insulin or somatostatin gene. Exemplary tissue-specific elements include the rat insulin-1 "P-Box" (SEQ ID NO:8) (i.e., nucleotide positions −82 to −64 of the rat insulin gene described in Ohlsson and Edlund, 1986, *Cell*, 45:35–44, incorporated herein by reference); the rat insulin-1 "FLAT" or "E2" response element (SEQ ID NO:9)(i.e., nucleotide positions −222 to −208 of the rat insulin gene described in Ohlsson and Edlund, supra); TSE-I (SEQ ID NO:3); TSE-II (SEQ ID NO:4); and the like. In a particularly preferred embodiment, the invention transcription factor has the ability to bind each of the above-described response elements.

The phrase "pancreatic islet hormone gene" refers to a hormone-encoding gene that is endogenous to endocrine pancreatic islet cells. The term "pancreatic islets" refers to a population of cells derived from a mammalian endocrine pancreas (islet cells). Such cells synthesize and secrete the peptide hormones glucagon (pancreatic A-cells), insulin (pancreatic B-cells), somatostatin (pancreatic D-cells), and pancreatic polypeptide (pancreatic F-cells).

The invention transcription factors are characterized by having the ability to bind to a plurality of promoters that control hormone gene expression in pancreatic islet cells (i.e., ability to bind to more than one hormone gene promoter). Preferably, the invention transcription factor modulates RNA transcription from at least the insulin and somatostatin genes. The invention transcription factor can modulate transcription either by trans-activating or trans-repressing RNA transcription.

In a particular embodiment, the invention transcription factors are further characterized by having the ability to trans-activate pancreatic hormone gene expression, e.g., activate expression of insulin, glucagon and somatostatin, within the pancreas and small intestine. The term "trans-activate", or grammatical variations thereof, as it relates to hormone gene expression, refers to the action of the invention transcription factor in binding to the promoter region of a pancreatic islet hormone gene and cooperating in the initiation of mRNA transcription.

In another embodiment, the invention transcription factors are further characterized by having the ability to trans-repress pancreatic hormone gene expression, e.g., repress expression of insulin, glucagon and somatostatin, within the pancreas and small intestine. The term "trans-repress", or grammatical variations thereof, as it relates to hormone gene expression, refers to the action of the invention transcription factor, or polypeptide fragment thereof, in binding to the promoter region of a pancreatic islet hormone gene and inhibiting in the initiation of mRNA transcription (i.e., eliminating RNA transcription activity from the promoter).

In another aspect, the invention transcription factor is a tissue-specific regulator of insulin and somatostatin transcription, particularly in small intestine and pancreas. Expression of the naturally occurring invention protein is highly restricted to endocrine cell types within the pancreas and small intestine where it constitutes the major binding activity at functionally important cis elements on the insulin and somatostatin promoters. The invention protein has been found to stimulate transcription (i.e, trans-activate) in vitro and in vivo through the same cis elements.

Remarkably, the invention transcription factor accounts for the predominant TSE binding activity in nuclear extracts from insulin and somatostatin producing pancreatic islet cells, supporting the proposition that this protein plays a primary role in regulating peptide hormone expression and in specifying endocrine cell lineage in the developing gut.

Since CREB constitutes the major CRE binding activity in Tu-6 cells, it is believed that cooperativity, which is observed in vivo, may arise from interactions between CREB and invention pancreatic transcription factor. In the absence of hormonal stimulation, CREB activity does not appear to arise from the cAMP-regulated PK-A site but from a glutamine rich domain termed Q2. Thus, CREB may subserve several functions by alternatively employing phosphorylation-dependent or constitutive activation domains which act in synergy with the invention cell-specific transcription factors to provide high level expression of pancreatic hormone genes, such as the insulin and somatostatin genes.

In yet another embodiment of the present invention, the invention transcription factors are further characterized by being uniformly expressed in B-cells and D-cells of the endocrine pancreas and not expressed in exocrine cells.

As used herein, the phrase "uniformly expressed" means that naturally occurring RNA encoding the invention transcription factor protein can be detected in each of the pancreatic islet cell types that produce insulin and somatostatin. Preferably, the level of expression is substantially equal in each of these pancreatic islet cell types.

In another aspect, the invention transcription factor protein is further characterized by being responsive to fluctuations in glucose concentration. As used herein, the phrase "responsive to fluctuations in glucose concentration", means that the expression of the invention transcription factor varies relative to the glucose concentration present. For example, the level of mRNA encoding the invention protein is substantially higher when pancreatic islet cells are cultured in about 20 mM glucose than when pancreatic islet cells are cultured in about 2 mM glucose.

Presently preferred pancreatic islet hormone transcription factor proteins of the invention have amino acid sequences that are substantially the same as the protein sequence set forth in SEQ ID NO:2, and amino acid sequences which are substantially the same as the amino acid sequences encoded by the transcription factor-encoding portion of plasmid pITF-1, deposited with the ATCC under accession number 69385, as well as biologically active, modified forms thereof. Those of skill in the art will recognize that numerous residues of the above-described sequences can be substituted with other, chemically, sterically and/or electronically similar residues without substantially altering the biological activity of the resulting receptor species.

The plasmid pITF-1 transformed in *E. coli* XL1-Blue cells (Stratagene) was deposited Aug. 12, 1993, at the American Type Culture Collection (ATCC), 12301 Parklawn Drive, Rockville, Md., U.S.A. 20852, under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted. In particular, upon issuance of a U.S. patent based on this or any application claiming priority to or incorporating this application by reference thereto, all restriction upon availability of the deposited material will be irrevocably removed.

As employed herein, the term "substantially the same amino acid sequence" refers to amino acid sequences having at least about 70% identity with respect to the reference amino acid sequence, and retaining comparable functional and biological activity characteristic of the protein defined by the reference amino acid sequence. Preferably, proteins having "substantially the same amino acid sequence" will have at least about 80%, more preferably 90% amino acid identity with respect to the reference amino acid sequence; with greater than about 95% amino acid sequence identity being especially preferred.

The term "biologically active" or "functional", when used herein as a modifier of invention transcription factor protein (s), or polypeptide fragment thereof, refers to a polypeptide that exhibits functional characteristics similar to any of the homeobox-type transcription factors described herein. For example, in one embodiment, biologically active proteins are those that bind to either TSE-I, TSE-II, "P-Box", "FLAT" and modulate the transcription of RNA therefrom. Such activity may be assayed by any method known to those of skill in the art including, but not limited to, the Gel Shift and DNAse I Protection Assays described in Example 5.

The invention transcription factor proteins can be isolated by a variety of methods well-known in the art, e.g., the methods described in Examples 1–3, the recombinant expression systems described hereinafter, and the like.

In accordance with another embodiment of the present invention, there is provided an isolated nucleic acid encoding an invention transcription factor protein. The nucleic acid molecules described herein are useful for producing invention transcription factor proteins, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of a pancreatic hormone transcription factor gene or mRNA transcript in a given sample. The nucleic acid molecules described herein, and fragments thereof, are also useful as primers and/or templates in a PCR reaction for amplifying genes encoding the invention transcription factor protein described herein.

An exemplary nucleic acid encoding an endocrine transcription factor may be selected from:

(a) DNA encoding the amino acid sequence set forth in SEQ ID NO:2, or the transcription factor-encoding portion of plasmid pITF-1, deposited with the ATCC under accession number 69385, (b) DNA that hybridizes to the DNA of (a) under moderately stringent conditions, wherein said DNA encodes biologically active endocrine hormone transcription factor, or (c) DNA degenerate with respect to either (a) or (b) above, wherein said DNA encodes biologically active endocrine hormone transcription factor.

As employed herein, the phrase "nucleic acid" refers to ribonucleic acid (RNA) or deoxyribonucleic acid (DNA). DNA can be either complementary DNA (cDNA) or genomic DNA, e.g. a gene encoding an endocrine transcription factor.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60%, preferably about 75%, more preferably about 85%, homology to the target DNA; with greater than about 90% homology to target-DNA being especially preferred. Preferably, moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 65° C.

The phrase "high stringency hybridization" refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5×Denhart's solution, 6×SSPE, 0.2% SDS at 42° C., followed by washing in 1×SSPE, 0.2% SDS, at 50° C. Denhart's solution and SSPE (see, e.g., Sambrook et al., *Molecular Cloning, A Laboratory Manual*, Cold Spring Harbor Laboratory Press, 1989) are well known to those of skill in the art as are other suitable hybridization buffers.

As used herein, the term "degenerate" refers to codons that differ in at least one nucleotide from a reference nucleic acid, e.g., SEQ ID NO:1, but encode the same amino acids as the reference nucleic acid. For example, codons specified by the triplets "UCU", "UCC", "UCA", and "UCG" are degenerate with respect to each other since all four of these codons encode the amino acid serine.

In a preferred embodiment, cDNAs encoding the endocrine hormone transcription factor proteins disclosed herein have substantially the same nucleotide sequence as nucleotides 331–1182 of SEQ ID NO:1 or the transcription factor-encoding portion of plasmid pITF-1, deposited with the ATCC under accession number 69385. The presently most preferred cDNA molecules encoding the endocrine hormone transcription factor proteins have the same nucleotide sequence as nucleotides 331–1182 of SEQ ID NO:1 or the transcription factor-encoding portion of plasmid pITF-1, deposited with the ATCC under accession number 69385.

As employed herein, the term "substantially the same nucleotide sequence" refers to DNA having sufficient homology to the reference polynucleotide, such that it will hybridize to the reference nucleotide under moderately stringent hybridization conditions. In one embodiment, DNA having substantially the same nucleotide sequence as the reference nucleotide sequence encodes substantially the same amino acid sequence as that set forth in SEQ ID NO:2. In another embodiment, DNA having "substantially the same nucleotide sequence" as the reference nucleotide sequence has at least 60% homology with respect to the reference nucleotide sequence. DNA having at least 70%, more preferably 90%, yet more preferably 95%, homology to the reference nucleotide sequence is preferred.

The invention nucleic acids can be produced by a variety of methods well-known in the art, e.g., the methods described in Examples 1 and 2, employing PCR amplification using oligonucleotide primers from various regions of SEQ ID NO:1, and the like.

In accordance with a further embodiment of the present invention, optionally labeled transcription factor-encoding cDNAs, or fragments thereof, can be employed to probe library(ies) (e.g., cDNA, genomic, and the like) for additional nucleic acid sequences encoding novel mammalian pancreatic islet hormone transcription factors. As described in Examples 1 and 2, construction of mammalian pancreatic islet cDNA libraries, preferably a human pancreatic islet cDNA library, is well-known in the art. Screening of such a cDNA library is initially carried out under low-stringency conditions, which comprise a temperature of less than about 42° C., a formamide concentration of less than about 50%, and a moderate to low salt concentration.

Presently preferred probe-based screening conditions comprise a temperature of about 37° C., a formamide concentration of about 20%, and a salt concentration of about 5×standard saline citrate (SSC; 20×SSC contains 3M sodium chloride, 0.3M sodium citrate, pH 7.0). Such conditions will allow the identification of sequences which have a substantial degree of similarity with the probe sequence, without requiring perfect homology. The phrase "substantial similarity" refers to sequences which share at least 50% homology. Preferably, hybridization conditions will be selected which allow the identification of sequences having at least 70% homology with the probe, while discriminating against sequences which have a lower degree of homology with the probe. As a result, nucleic acids having substantially the same nucleotide sequence as nucleotides 331–1182 of SEQ ID NO:1 are obtained.

As used herein, a nucleic acid "probe" is single-stranded DNA or RNA, or analogs thereof, that has a sequence of nucleotides that includes at least 14, preferably at least 20, more preferably at least 50, contiguous bases that are the same as (or the complement of) any 14 or more contiguous bases set forth in any of SEQ ID NO:1, preferably nucleotides 331–1182. Preferred regions from which to construct probes include 5' and/or 3' coding regions of SEQ ID NO:1. In addition, the entire cDNA encoding region of an invention transcription factor protein may be used as a probe. Probes may be labeled by methods well-known in the art, as described hereinafter, and used in various diagnostic kits.

As used herein, the terms "label" and "indicating means" in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturation to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalenesulfonyl chloride (DANSC), tetramethylrhodamine isothiocyanate (TRITC), lissamine, rhodamine 8200 sulfonyl chloride (RB-200-SC), and the like. A description of immunofluorescent analytic techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

In one embodiment, the indicating group is an enzyme, such as horseradish peroxidase (HRP), glucose oxidase, and the like. In such cases where the principal indicating group is an enzyme, additional reagents are required for the production of a visible signal. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

In another embodiment, radioactive elements are employed labeling agents. An exemplary radiolabeling agent is a radioactive element that produces gamma ray emissions. Elements which emit gamma rays, such as $^{124}I$, $^{125}I$, $^{126}I$, $^{131}I$ and $^{51}Cr$, represent one class of radioactive element indicating groups. Particularly preferred is $^{125}I$. Another group of useful labeling means are those elements such as $^{11}C$, $^{18}F$, $^{15}O$ and $^{13}N$ which emit positrons. The positrons so emitted produce gamma rays upon encounters with electrons present in the animal's body. Also useful is a beta emitter, such as $^{32}P$, $^{111}$indium or $^{3}H$.

The linking of a label to a substrate, i.e., labeling of nucleic acid probes, antibodies, polypeptides, and proteins, is well known in the art. For instance, an invention antibody can be labeled by metabolic incorporation of radiolabeled amino acids provided in the culture medium. See, for example, Galfre et al., Meth. Enzymol., 73:3–46 (1981). Conventional means of protein conjugation or coupling by activated functional groups are particularly applicable. See, for example, Aurameas et al., Scand. J. Immunol., Vol. 8, Suppl. 7:7–23 (1978), Rodwell et al., Biotech., 3:889–894 (1984), and U.S. Pat. No. 4,493,795.

In accordance with yet another embodiment of the present invention, there is provided a method for the recombinant production of invention transcription factor(s) by expressing the above-described nucleic acid sequences in suitable host cells. Recombinant DNA expression systems that are suitable to produce pancreatic transcription factors described herein are well-known in the art. For example, the above-described nucleotide sequences can be incorporated into vectors for further manipulation. As used herein, vector (or plasmid) refers to discrete elements that are used to introduce heterologous DNA into cells for either expression or replication thereof.

Suitable expression vectors include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that are replicable in eukaryotic cells and/or prokaryotic cells and those that remain episomal or those which integrate into the host cell genome.

As used herein, a promoter region refers to a segment of DNA that controls transcription of DNA to which it is operatively linked. The promoter region includes specific sequences that are sufficient for RNA polymerase recognition, binding and transcription initiation. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector nucleotide sequences, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potentially inappropriate alternative translation initiation (i.e., start) codons or other sequences that may interfere with or reduce expression, either at the level of transcription or translation. Alternatively, consensus ribosome binding sites (see, for example, Kozak (1991) J. Biol. Chem. 266:19867–19870) can be inserted immediately 5' of the start codon and may enhance expression. The desirability of (or need for) such modification may be empirically determined.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Prokaryotic transformation vectors are well-known in the art and include pBlueskript and phage Lambda ZAP vectors (Stratagene, La Jolla, Calif.), and the like. Other suitable vectors and promoters are disclosed in detail in U.S. Pat. No. 4,798,885, issued Jan. 17, 1989, the disclosure of which is incorporated herein by reference in its entirety. In addition, expression cassettes, which include sequences, such as the 5' region of the lac Z gene (including the operator, promoter, transcription start site, Shine-Delgarno sequence and translation initiation signal), the regulatory region from the tryptophan gene (trp operator, promoter, ribosome binding site and translation initiator), and a fusion gene containing two promoters called the tap-lac or commonly called the Tac promoter, are available into which synthetic DNA may be conveniently inserted before the cassette is inserted into a cloning vector of choice.

Other suitable vectors for transformation of E. coli cells include the pET expression vectors (Novagen, see U.S. Pat. No. 4,952,496), e.g., pET11a, which contains the T7 promoter, T7 terminator, the inducible E. coli lac operator, and the lac repressor gene; and pET 12a–c, which contain the T7 promoter, T7 terminator, and the E. coli ompT secretion signal. Another suitable vector is the pIN-IIIompA2 (see Duffaud et al., Meth. in Enzymology, 153:492–507, 1987), which contains the lpp promoter, the lacUV5 promoter operator, the ompA secretion signal, and the lac repressor gene. A preferred expression vector is the PGEX-2T vector (Pharmacia) described in Example 3.

Exemplary, eukaryotic transformation vectors, include the cloned bovine papilloma virus genome, the cloned genomes of the murine retroviruses, and eukaryotic cassettes, such as the pSV-2 gpt system [described by Mulligan and Berg, Nature Vol. 277:108–114 (1979)] the Okayama-Berg cloning system [Mol. Cell Biol. Vol. 2:161–170 (1982)], and the expression cloning vector described by Genetics Institute [Science Vol. 228:810–815 (1985)], are available which provide substantial assurance of at least some expression of the protein of interest in the transformed eukaryotic cell line.

Particularly preferred base vectors which contain regulatory elements that can be linked to the invention transcription factor-encoding DNAs for transfection of mammalian cells are cytomegalovirus (CMV) promoter-based vectors such as pcDNA1 (Invitrogen, San Diego, Calif.), MMTV promoter-based vectors such as pMAMNeo (Clontech, Palo Alto, Calif.) and pMSG (Pharmacia, Piscataway, N.J.), and SV40 promoter-based vectors such as pSVβ (Clontech, Palo Alto, Calif.).

In accordance with another embodiment of the present invention, there are provided "recombinant cells" containing the nucleic acid molecules (i.e., DNA or mRNA) of the present invention. Methods of transforming suitable host cells, preferably bacterial cells, and more preferably *E. coli* cells, as well as methods applicable for culturing said cells containing a gene encoding a heterologous protein, are generally known in the art. See, for example, Sambrook et al., *Molecular Cloning: A Laboratory Manual* (2 ed.), Cold Spring Harbor Laboratory Press, Cold Spring Harbor, N.Y., USA (1989).

Exemplary methods of transformation include, e.g., transformation employing plasmids, viral, or bacterial phage vectors, transfection, electroporation, lipofection, and the like. The heterologous DNA can optionally include sequences which allow for its extrachromosomal maintenance, or said heterologous DNA can be caused to integrate into the genome of the host (as an alternative means to ensure stable maintenance in the host).

Host organisms contemplated for use in the practice of the present invention include those organisms in which recombinant production of heterologous proteins has been carried out. Examples of such host organisms include bacteria (e.g., *E. coli*), yeast (e.g., *Saccharomyces cerevisiae, Candida tropicalis, Hansenula polymorpha* and *P. pastoris*; see, e.g., U.S. Pat. Nos. 4,882,279, 4,837,148, 4,929,555 and 4,855, 231), mammalian cells (e.g., HEK293, CHO and Ltk⁻ cells), insect cells, and the like. Presently preferred host organisms are bacteria. The most preferred bacteria is *E. coli*.

In accordance with yet another embodiment of the present invention, there are provided antibodies raised against the invention pancreatic transcription factor. Such antibodies can be prepared employing standard techniques, as are well known to those of skill in the art, using invention proteins, or fragments thereof, as antigens for antibody production (see, e.g., Example 6). Antibodies of the present invention are typically produced by immunizing a mammal with an inoculum containing an invention transcription factor protein or fragment thereof and thereby inducing the production of antibody molecules having immunospecificity for the immunizing agent.

For example, antibodies raised in rabbits against a synthetic peptide fragment of the invention protein recognize the synthetic peptide and the corresponding invention transcription factor protein on an equimolar basis, and preferably, are capable of inhibiting the activity of the native protein. Antibodies to invention protein may be obtained, for example, by immunizing three month old male and female white New Zealand rabbits with a suitable synthetic peptide fragment to which Tyr has been added at the C-terminus in order to couple it, as an antigen, to BSA by a bisdiazotized benzidine (BDB) linkage by reaction for 2 hours at 4° C. The reaction mixture is dialyzed to remove low molecular weight material, and the retained material is frozen in liquid nitrogen and stored at −20° C. Animals are immunized with the equivalent of 1 mg of the peptide antigen according to the procedure of Benoit et al. *P.N.A.S. USA*, 79, 917–921 (1982). At four week intervals, the animals are boosted by injections of 200 μg of the antigen and bled ten to fourteen days later. After the third boost, antiserum is examined for its capacity to bind radioiodinated antigen peptide prepared by the chloramine-T method and then purified by CMC-ion exchange column chromatography. The antibody molecules are then collected from the mammal and isolated to the extent desired by well known techniques such as, for example, by using DEAE Sephadex to obtain the IgG fraction.

To enhance the specificity of the antibody, the antibodies may be purified by immunoaffinity chromatography using solid phase-affixed immunizing polypeptide. The antibody is contacted with the solid phase immunizing polypeptide for a period of time sufficient for the polypeptide to immunoreact with the antibody molecules to form a solid phase immunocomplex. The bound antibodies are then separated from the complex by standard techniques. An exemplary anti-pancreatic hormone transcription factor antibody that is immunoreactive with amino acids 196–214 of SEQ ID NO:2 is described in Example 6.

Antibody so produced can be used, inter alia, in diagnostic methods and systems to detect the level of pancreatic islet transcription factor protein present in a mammalian, preferably human, body sample, such as tissue or vascular fluid. Such antibodies can also be used for the immunoaffinity or affinity chromatography purification of the invention transcription factor protein.

In accordance with yet another embodiment of the present invention, there is provided a method to regulate transcription from a promoter controlling a pancreatic hormone gene, said method comprising:

contacting said promoter with an invention transcription factor protein.

As used herein, the term "contacting" refers to providing, in a suitable environment (e.g., appropriate buffer or physiological conditions) an invention transcription factor, or DNA-binding fragment thereof, for a period of time sufficient for the transcription factor protein to bind with a tissue-specific promoter element from a pancreatic hormone gene promoter, preferably the insulin gene promoter. Such contacting can occur in either cell-free in vitro systems, cells cultured in vitro, or in vivo within any cell containing a gene encoding a biologically active insulin protein.

In accordance with yet another embodiment of the present invention, there is provided a method for modulating the level of insulin in a mammal, said method comprising:

contacting, in the presence of glucose, a gene encoding a biologically active insulin protein with an invention transcription factor protein, or DNA-binding fragments thereof.

The phrase "in the presence of glucose" means that glucose is present in sufficient concentrations such that glucose-responsive expression of the invention transcription factor protein occurs. For example, in patients with chronic elevation of glucose levels significantly above the normal range of 80–90 mg/ml vascular fluid, glucose-responsive expression of the invention transcription factor protein occurs.

For the practice of the present therapeutic methods, invention nucleic acids encoding the pancreatic transcription factor protein are introduced into appropriate cells that are capable of expressing biologically active insulin, such as pancreatic islets B-cells. Since it has been found that the invention homeobox-type transcription factor transactivates the expression of the insulin gene, it is believed that causing the expression of the invention transcription factor protein will thereby cause expression of insulin in a given cell containing an insulin gene. In addition, because it has been found that the expression level of the invention transcription factor protein is responsive to varying concentrations of glucose, the invention methods provide a means for glucose-responsive expression of insulin.

Invention nucleic acids can be introduced into such cells either in vivo, or introduced into cells cultured in vitro prior to transplanting the cells into a patient in need thereof. The invention nucleic acids can be introduced, in vitro, into an appropriate endocrine cell using any of the methods described above for making recombinant cells.

Methods of transplanting pancreatic cells are well-known in the art. See, for example, U.S. Pat. Nos. 4,997,443 and 4,902,295, which describe a transplantable artificial tissue matrix structure containing viable cells, preferably pancreatic islet cells, suitable for insertion into a human. Cell-encapsulated transplantation methods that protect the transplanted cell against the host immune response are well-known in the art (see, e.g., U.S. Pat. Nos. 4,353,888 and 4,696,286). Thus, any human cell that is able to process insulin, preferably an endocrine cell, is contemplated for use in the therapeutic methods described herein.

For example, mammalian primary fetal islet cells, preferably human, may be isolated and transduced with an appropriate vector, or multiple vectors, containing nucleic acid encoding the invention transcription factor and/or a gene encoding a biologically active insulin protein such that glucose-responsive expression of the invention transcription factor protein is ensured, thereby causing the glucose-responsive expression of insulin. In addition, see, U.S. Pat. No. 4,935,000, which describes methods for inducing epithelium cells to differentiate into islet cells; and U.S. Pat. No. 4,868,121, which describes methods for producing islet of Langerhans capable of producing biologically active insulin.

In one embodiment, nucleic acids encoding the invention transcription factor proteins can be delivered into mammalian cells, preferably pancreatic islet cells, either in vivo or in vitro using suitable viral vectors well-known in the art. Suitable retroviral vectors, designed specifically for in vivo "gene therapy" methods, are described, for example, in WIPO publications WO 9205266 and WO 9214829, which provide a description of methods for efficiently introducing nucleic acids into human cells in vivo. In addition, where it is desirable to limit or reduce the in vivo expression of the invention transcription factor, the introduction of the antisense strand of the invention nucleic acid is contemplated.

As used herein, "gene encoding a biologically active insulin protein" refers to a gene encoding insulin protein such that when expressed in-vivo the protein is capable of regulating the concentration of glucose in a physiologically normal manner.

In accordance with yet another embodiment of the present invention, there is provided a method for treating diabetes in a mammal, said method comprising:

expressing, in the presence of glucose, an invention nucleic acid vector in a cell containing a gene encoding a biologically active insulin protein.

The invention will now be described in greater detail by reference to the following non-limiting examples. All U.S. patents and all publications mentioned herein are incorporated in their entirety by reference thereto.

Unless otherwise stated, the present invention was performed using standard procedures, as described, for example in Maniatis et al., *Molecular Cloning: A Laboratory Manual*, Cold Spring Harbor Laboratory Press, Cold Spring Harbor, N.Y., USA (1982); Sambrook et al., *Molecular Cloning: A Laboratory Manual* (2 ed.), Cold Spring Harbor Laboratory Press, Cold Spring Harbor, N.Y., USA (1989); Davis et al., *Basic Methods in Molecular Biology*, Elsevier Science Publishing, Inc., N.Y., USA (1986); or *Methods in Enzymology: Guide to Molecular Cloning Techniques* Vol.152, S. L. Berger and A. R. Kimmerl Eds., Academic Press Inc., San Diego, USA (1987).

The Tu6 cell line was derived from a pancreatic tumor (see Madsen et al., 1986, *J. Cell Biol.*, 103:2025–2034). It is believed that the invention cDNAs can be obtained from any pancreatic islet cell source employing methods well-known in the art. In all cases, CAT activity was measured after normalizing to activity of a co-transfected RSV-luciferase reporter plasmid. CMV-ITF-1 expression plasmids were constructed by inserting the ITF-1 cDNA into a CMV promoter containing parent plasmid (e.g., pOG44, commercially available from Stratagene, La Joll, Calif.) using standard cloning procedures. "-TSE" and "4×TSE" somatostatin plasmids were prepared as described in Leonard et al., (1992) PNAS, 89:6247–6251.

EXAMPLE 1

Tu6 cDNA library construction

Tu6 cDNA was synthesized from 5 μg of Tu6 cell-derived poly(A)-selected RNA using a TimeSaver cDNA synthesis Kit (Pharmacia). Not I/Eco RI adapters with Eco RI overhangs were ligated onto the cDNA ends, and unincorporated linkers were separated from the cDNA by chromatography with a CL-4B sepharose column (Pharmacia). cDNAs of 1.5-4 kb were size-selected by agarose gel electrophoresis and ligated into λgt-11 phage arms. After packaging with Gigapack II Gold (Stratagene), the library contained $4 \times 10^6$ pfu, with less than 2% corresponding to religated phage arms as determined by blue/white color selection.

EXAMPLE 2

Isolation of cDNAs encoding homeobox-type transcription factor protein

Homeobox sequences were isolated from the phage Tu-6 cDNA library by PCR amplification with degenerate oligonucleotide primers encoding amino acids LEKEF (sense orientation, aa. 17–21 of the homeodomain) and IWFQN (antisense orientation, aa. 48–52). The synthetic primers employed were 5'-GGCGGATCCCTXRARARRGART(A/T)C-3' (SEQ ID NO:5) and 5'GGCGGATCCC(G/T)RTTYTGRAACCA-3' (SEQ ID NO:6), where R=A/G AND Y=C/T. PCR was performed using 20 pmol of each primer and 1 ng Tu6 cDNA. Annealing temperature was 45° C. for three cycles followed by 55° C. for 35 cycles. The anticipated PCR product of 129 bp was resolved by agarose gel electrophoresis, excised from the gel, subcloned into Bluescript SK II, and analyzed by double-stranded DNA sequencing. Six amplified DNA fragments of predicted size were obtained and were subcloned into Bluescript SKII. Of 6 recombinant clones analyzed, 5 corresponded to the same homeodomain fragment.

To obtain full-length ITF-1 cDNA clones, the ITF-1 PCR fragment was labeled to high specific activity by random primer labeling. Approximately $10^6$ plaques from a Tu-6 λgt11 library were screened by hybridization to the ITF-1 fragment probe. Thirty positive plaques were purified, and several of these were subcloned into Bluescript SK II and sequenced on both strands. A full-length 1.6 kb cDNA clone was obtained that encodes a novel protein of 283 amino acids, which has been termed insulin transcription factor-1 or ITF-1 (SEQ ID NO:1).

EXAMPLE 3
Expression of homeobox-type transcription factor protein in *E. coli*.

The 1.6 kb ITF-1 cDNA sequence, described in Example 2 above, was inserted in frame into the bacterial expression vector pGEX-2T (Pharmacia). The resultant expression plasmid, labeled "pITF-I", was introduced into *E. coli* strain BL 21. Cells were grown in 1 liter of LB media (see Sambrook et al., supra) plus 30 µg/ml ampicillin, to an OD $A_{600}$ of 0.6. Cells were induced with 0.25 g IPTG (isopropyl-β-D-thiogalactopyranoside) for 3 hours, centrifuged, and resuspended in HDB buffer (140 mM NaCl, 5 mM KCl, 0.7 mM $Na_2HPO_4$, 25 mM Hepes pH7.4) containing protease inhibitors (1 mM PMSF, trasylol, and 100 U/ml leupeptin). Cells were lysed by treatment with lysozyme (1 mg/ml) for 30 minutes on ice. Lysis solution was then added such that the extract contained final concentrations of 1% Triton X-100, 5 mM EDTA, 1 mM DTT, 1M NaCl. The lysate was centrifuged 30 minutes at 40K g, and the supernatant was dialyzed in HDB buffer containing 1% triton, protease inhibitors, and DTT at 1 mM for 2 hours. The lysate was then mixed with 500 µl glutathione-agarose beads for 20 minutes at 4° C. The beads were washed seven times, and isolated and pure recombinant ITF-1 protein was eluted by incubating the beads with 7 units of thrombin for 1 hour at room temperature.

EXAMPLE 4
RNAse protection and in situ hybridization analysis

To determine whether production of the invention transcription factor protein is limited to endocrine cell types associated with insulin and somatostatin production, RNAse protection assays were performed on RNAs obtained from a variety of cell lines and tissues. RNA was prepared from 11 rat cell lines and 11 adult rat tissues derived from hypothalamus, cerebellum, midbrain, brainstem, small intestine, cortex, pancreas, heart, kidney, liver, and spleen, by a standard acid/guanidinium/phenol procedure (see Sambrook, supra). For RNAse protection analysis, a Hind III-linearized plasmid riboprobe was used containing a 318 bp fragment of ITF-1 cDNA corresponding to amino acids 60–165 of SEQ ID NO:1. The riboprobe was annealed to 30 µg total RNA and processed as described in Leanord et al., supra. ITF-1 RNA was observed in both Tu-6 and RIN5 AH pancreatic islet cell lines, but no detectable ITF-1 RNA was observed in non-endocrine-islet cell lines including PC12, JEG-3, COS, HT 22, Hela, and others. Of the 11 rat tissues that were examined, only pancreas and small intestine contained ITF-1 RNA, demonstrating that the corresponding invention transcription factor protein is highly restricted to endocrine cells of the small intestine and pancreas.

The sites of ITF-1 RNA production were also determined by in situ hybridization. For in situ hybridizations, pancreas and small intestine were sectioned on a cryostat, mounted onto slides, and hybridized with ITF-1 antisense riboprobe (See, e.g., Lee et al., (1990) *Mol. and Cellular Neuroscience*, 1:168–177. Using a $^{35}$S-labeled ITF-1 antisense riboprobe, ITF-1 RNA was detected in islets, but not in surrounding exocrine acinar cells. Within the islet, the hybridization signal was evenly distributed over all cells. Since only 10–20% of islet cells produce somatostatin, it is believed that other cell types such as insulin containing β-cells also express this factor. ITF-1 RNA was present in most epithelial cells of the small intestine, but only a small number of these was found to produce somatostatin. Thus in both tissues, somatostatin producing cells appear to account for only a small subset of those expressing ITF-1.

EXAMPLE 5
Gel mobility shift and DNAse I protection analysis

Within the rat insulin promoter, two tissue-specific elements, termed "P-Box" (SEQ ID NO:8) and "FLAT" or "E2" (SEQ ID NO:9), are involved in promoting insulin expression in pancreatic islet cells. Within the somatostatin promoter, two related tissue-specific elements, termed TSE I (SEQ ID NO:3) and TSE II (SEQ ID NO:4), promote somatostatin expression in pancreatic islet Tu-6 cells. To determine whether ITF-1 could bind to these functionally defined elements, recombinant ITF-1 protein was prepared from *E. coli* transformed with a prokaryotic GST-ITF-1 expression plasmid (described in Example 3). After purification on glutathione-agarose beads, the GST-ITF-1 fusion protein was cleaved with thrombin, permitting retrieval of a 161 amino acid ITF-1 polypeptide fragment extending from amino acids. 124–283 of SEQ ID NO:2.

DNAse I protection studies with somatostatin promoter fragments were performed (see Yamamoto et al., 1990, *Cell*, 60:611–617) using double-stranded somatostatin TSE I and TSE II oligos extending from −104 to −86 (5'-TTGCGAGGCTAATGGTGCG-3, SEQ ID NO:3) and −303 to −281 (5'-GATCTCAGTAATAATCATGCAG-3', SEQ ID NO:4), respectively. Mutant TSE I was as prepared as described in Leonard et al., supra, and TSE II oligo contained 5'-GATCTCAGGCCGGCCGCATGCAC-3' (SEQ ID NO:7). Discreet footprints over both TSE I and TSE II sites were observed. Protection at both sites coincided with the footprinting patterns obtained using crude Tu-6 nuclear extracts. The TSE II site was completely protected at far lower concentrations of ITF-1, suggesting that this site might bind this protein with higher affinity than the TSE I site.

Similar DNAase I protection assays were conducted using double-stranded oligonucleotides corresponding to the rat insulin I tissue-specific promoter fragments "P-Box" (SEQ ID NO:8) and "FLAT" (SEQ ID NO:9) (See Ohlsson and Edlund, supra). Similar to the results obtained for the somatostatin promoter fragments, discreet footprints over both insulin promoter "P-Box" and "FLAT" sites were observed in assays conducted with recombinant ITF-1 protein.

Gel mobility shift assays (see, e.g., Yamamoto et al., supra) using labeled TSE I and TSE II oligos were conducted to evaluate the DNA binding properties of ITF-1. The results indicate that binding of recombinant ITF-1 protein to either site was readily displaced by an excess of unlabeled wild-type TSE I or TSE II competitor DNAs. However, mutant versions of TSE I and TSE II with substitutions in the TAAT recognition motif could not compete for ITF-1 binding. As with footprinting studies, the affinity of ITF-1 protein for TSE II appeared to be higher than for TSE I.

Similar Gel mobility shift assays were conducted using double-stranded oligonucleotides corresponding to the rat insulin I tissue-specific promoter fragments "P-Box" and "FLAT" (See Ohlsson and Edlund, supra). The results indicate that binding of recombinant ITF-1 protein to either site was readily displaced by an excess of unlabeled wild-type P-Box or FLAT competitor DNAs. However, mutant versions of P-Box and FLAT could not compete for ITF-1 binding.

The relative abundance of ITF-1 DNA-binding to other DNA-binding activities in somatostatin expressing cells was assayed by gel shift experiments with Tu-6 nuclear extracts. Using the high affinity TSE II probe, three complexes were observed, termed C1, C2, and C3, based on their relative mobility. Complexes C1 and C3 appeared with low amounts of extract, whereas complex C2 emerged when higher concentrations of extract were employed. C1 and C2 would appear to represent high affinity complexes since both were displaced by wild-type but not mutant TSE I and TSE II oligos. As neither C1 nor C2 were observed in non-endocrine-islet cell extracts such as Hela, these complexes would also appear to be tissue specific.

EXAMPLE 6
Antibodies and Western blot analysis

To determine whether the C1, C2, and C3 complexes (described in Example 5) might contain factors related to ITF-1, a rabbit polyclonal antiserum (anti-ITF-1) was developed against a synthetic ITF-1 peptide extending from amino acids 196–214 of SEQ ID NO:2. The anti-ITF-1 antiserum specifically recognizes recombinant ITF-1 protein in Western blot analysis. Western blot analysis with ITF-1 antiserum was performed on cytoplasmic and nuclear Tu-6 extracts (see, e.g., Leonard et al., supra).

In Tu-6 extracts, ITF-1 antiserum specifically recognized a 49 kD protein in nuclear and cytoplasmic extracts. Although the molecular weight of this band is quite different from the predicted mass of ITF-1 (31 kD), the 49 kD immunoreactive product co-migrates with the in-vitro translation product from reticulocyte lysates programmed with ITF-1 RNA.

As predicted from Western blot data showing ITF-1 protein in both nuclear and cytoplasmic fractions, complex C1 was observed in both extracts (cytoplasmic and nuclear) suggesting that this protein may leak out during extract preparation. When pre-incubated with Tu-6 nuclear extract, the ITF-1 antiserum completely abolished C1 and C2 complexes but had no effect on C3. As pre-immune serum had no effect on any of these complexes, our results suggest that ITF-1 protein accounts for the majority of TSE binding activity in Tu-6 cells.

Moreover, complex C1 had the same relative mobility as full-length recombinant ITF-1 protein -TSE complex further suggesting that C1 contains ITF-1. The appearance of C2 with increasing concentrations of Tu-6 nuclear extract indicates that this complex could be due to a dimeric form of ITF-1. Indeed the TSE II site contains 2 TAAT motifs which may encourage cooperative binding between two homeodomain monomers on this site.

When tested in gel mobility shift assays, the ITF-1 antiserum specifically inhibited the binding of recombinant ITF-1, but not ISL-1 protein, to the TSE probes.

EXAMPLE 7
In vitro transcription

The effect of recombinant ITF-1 on transcription from the insulin and somatostatin promoters was analyzed by in vitro transcription assays as previously described (see, e.g., Gonzalez et al., (1991) Mol. & Cell. Biol., 11(3):1306–1312) except that HeLa nuclear extracts were used in the place of PC12 extracts. ITF-1 and CREB proteins were evaluated separately and in unison. Hela nuclear extracts lack detectable amounts of ITF-1 protein, permitting the testing of this factor without interference from the endogenous protein.

Briefly, reactions were carried out in a final volume of 50 μl containing 10 mM HEPES pH 7.9, 60 mM KCl, 0.2 mM EDTA, 5 mM $MgCl_2$, 5% glycerol, 2% polyvinyl alcohol, 2 mM DTT, 100 ng pUCα1 (control DNA template), 200 ng somatostatin promoter template, 83 μg nuclear extract, and recombinant transcriptional activators "-TSE" and "4×TSE". The "-TSE" plasmid contains a minimal somatostatin promoter construct containing a CRE site but lacking TSE sites. The "4×TSE" plasmid is a somatostatin promoter vector containing 4 TSE I sites placed upstream of CRE site. The human α-globin template was used as internal control.

DNA templates, nuclear extract, and activator proteins were allowed to assemble for 30 min at 30° C. prior to the addition of all four ribonucleotides to final concentrations of 400 μM each. After an additional 30 min incubation, the reactions were terminated by extraction with phenol/chloroform/isoamyl alcohol [50:49:1] and analyzed by primer extension analysis (see, Gonzalez et al., supra). The extension product from the α-globin promoter is 64 nucleotides and from the somatostatin promoter is a doublet of 56 and 57 nucleotides.

Marked induction of somatostatin transcription after addition of purified ITF-1 protein was observed using a somatostatin promoter template containing 4 TSE I sites inserted upstream of the somatostatin CRE. In contrast, ITF-1 had no stimulatory effect on the α globin control promoter or on a somatostatin template lacking the TSE site (-TSE) at any level of protein tested. In contrast, purified CREB protein stimulated transcription from both -TSE and 4×TSE I templates.

To determine whether ITF-1 could also stimulate somatostatin transcription in vivo, ITF-1 cDNA was inserted into a cytomegalovirus (CMV) expression vector (e.g., pOG44, Stratagene) using standard methods. When examined in HeLa cells, the CMV-ITF-1 expression plasmid stimulated both TSE I and TSE II somatostatin reporter plasmids about 12-fold whereas a parent somatostatin promoter plasmid lacking these sites was only modestly affected. CMV-ITF-1 also stimulated TSE I and TSE II reporter activity upon co-transfection into PC12 cells, but the -TSE plasmid showed no induction. These results indicate that ITF-1 can specifically stimulate transcription from the somatostatin promoter in a cell-type independent manner.

Similar assays were conducted to evaluate the effect of recombinant ITF-1 on transcription from the rat insulin promoter. Likewise, the results indicate that ITF-1 can specifically stimulate transcription from the insulin promoter in a cell-type independent manner.

EXAMPLE 8
Effect of glucose concentration on endogenous gene expression of the invention homeobox-type transcription factor protein Pancreatic islet cells were cultured in the presence of varying concentrations of glucose ranging from 0–20 mM. Next, RNA was isolated from the various cultures of islet cells and probed with a cDNA fragment selected from SEQ ID NO:1.

The results indicate that in the presence of high glucose concentrations (i.e., about 20 mM), substantially higher levels of ITF-1 RNA were detected relative to the amount of ITF-1 RNA detected in the presence of low glucose concentrations (i.e., about 2 mM). Thus, the endogenous expression of the invention pancreatic transcription factor is responsive to fluctuations in glucose concentrations.

While the invention has been described in detail with reference to certain preferred embodiments thereof, it will be understood that modifications and variations are within the spirit and scope of that which is described and claimed.

SUMMARY OF SEQUENCES

Sequence ID No. 1 is the nucleic acid sequence (and the deduced amino acid sequence) of cDNA encoding an endocrine hormone transcription factor (ITF-1) of the present invention.

Sequence ID No. 2 is the deduced amino acid sequence of an endocrine hormone transcription factor (ITF-1) of the present invention.

Sequence ID No. 3 is TSE-I.

Sequence ID No. 4 is TSE-II.

Sequence ID No. 5 is a synthetic primer described in Example 2.

Sequence ID No. 6 is a synthetic primer described in Example 2.

Sequence ID No. 7 is a mutant TSE-II described in Example 5.

Sequence ID No. 8 is the insulin promoter "P-Box" region.

Sequence ID No. 9 is the insulin promoter "FLAT" (E2) region.

That which is claimed is:

1. An isolated nucleic acid encoding a mammalian insulin transcription factor protein, wherein said nucleic acid is selected from the group consisting of:
   a) nucleic acid encoding the amino acid sequence as set forth in SEQ ID NO:2;
   b) nucleic acid hybridizing under high stringency conditions to the complement of the nucleic acid as set forth in SEQ ID NO:1; and
   c) nucleic acid that is degenerate with the nucleic acid of a) or b).

2. A nucleic acid according to claim 1, wherein said nucleic acid comprises nucleotides 331–1182 set forth in SEQ ID No.1.

3. A nucleic acid according to claim 1, wherein said nucleic acid is cDNA.

4. A vector containing the nucleic acid of claim 1.

5. A host cell transfected or transformed with the vector of claim 4.

6. A host cell transfected or transformed with the nucleic acid of claim 1.

7. A method for expression of a homeobox-type pancreatic islet hormone transcription factor, said method comprising culturing the host cell of claim 6 under conditions suitable for expression of said transcription factor.

8. A method of producing a homeobox-type pancreatic islet hormone transcription factor comprising culturing the host cell of claim 6 under conditions suitable for expression of said transcription factor and recovering said transcription factor.

9. An isolated nucleic acid probe comprising at least 50 contiguous nucleotides of SEQ ID NO:1.

* * * * *

UNITED STATES PATENT AND TRADEMARK OFFICE
CERTIFICATE OF CORRECTION

PATENT NO. : 5,741,673
DATED : April 21, 1998
INVENTOR(S) : Marc R. Montimony, et. al.

It is certified that error appears in the above-identified patent and that said Letters Patent is hereby corrected as shown below:

In Column 14, line 19, "La Joll" should read --La Jolla--.

In Column 16, line 24, please delete the word "as" after the word "was".

Signed and Sealed this

Sixth Day of February, 2001

Attest:

Q. TODD DICKINSON

Attesting Officer

Director of Patents and Trademarks

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 1614 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 331..1182
        ( D ) OTHER INFORMATION: /product="ITF-1 Homeobox-type transcription factor"

( x i ) SEQUENCE DESCRIPTION: SEQ ID NO:1:

```
GAATTCCACG CGGCTGGTGG TGATAGGAGC CATGTTTTCT GCGTGCTCTG TCCGAGGTGC        60

TGAAAGAACT CCAGGCAGAT TCACCTGGAA GGACCCTGAA ACAAGGCTTC CAGGGGAAAC       120

ACGGGGGATC CGGGGACCGG CAGCGGCAGC GGGAGGGGCT GGAGGAAGGT CCGCGCTCTC       180

TATCAGCAAT GTGCCACCCT GCCCAGAGCA GTGGAGAACT GTCAAAGCGA TCTGGGGTGG       240

CGCTGAGAGT CCGTGAGCTG CCCAGCGCCT TAAGGCCTGG CTTGTAGCTC CCTACCCCGG       300

GCTGCCGGCC CCGAAGTGCC GGCTGCCACC ATG AAT AGT GAG GAG CAG TAC TAC        354
                                   Met Asn Ser Glu Glu Gln Tyr Tyr
                                    1               5

GCG GCC ACA CAG CTC TAC AAG GAC CCG TGC GCA TTC CAG AGG GGT CCG         402
Ala Ala Thr Gln Leu Tyr Lys Asp Pro Cys Ala Phe Gln Arg Gly Pro
         10                  15                  20

GTG CCA GAG TTC AGT GCT AAT CCC CCT GCG TGC CTG TAC ATG GGC CGC         450
Val Pro Glu Phe Ser Ala Asn Pro Pro Ala Cys Leu Tyr Met Gly Arg
 25                  30                  35                  40

CAG CCC CCA CCT CCG CCG CCA CCC CAG TTT GCA GGC TCG CTG GGA ACG         498
Gln Pro Pro Pro Pro Pro Pro Pro Gln Phe Ala Gly Ser Leu Gly Thr
                     45                  50                  55

CTG GAA CAG GGA AGT CCC CCG GAC ATC TCC CCA TAC GAA GTG CCC CCG         546
Leu Glu Gln Gly Ser Pro Pro Asp Ile Ser Pro Tyr Glu Val Pro Pro
                 60                  65                  70

CTC GCC GAT GAC CCG GCT GGC GCG CAC CTC CAC CAC CAC CTC CCA GCT         594
Leu Ala Asp Asp Pro Ala Gly Ala His Leu His His His Leu Pro Ala
             75                  80                  85

CAG CTC GGG CTC GCC CAT CCA CCT CCC GGA CCT TTC CCG AAT GGA ACC         642
Gln Leu Gly Leu Ala His Pro Pro Pro Gly Pro Phe Pro Asn Gly Thr
         90                  95                 100

GAG ACT GGG GGC CTG GAA GAG CCC AGC CGC GTT CAT CTC CCT TTC CCG         690
Glu Thr Gly Gly Leu Glu Glu Pro Ser Arg Val His Leu Pro Phe Pro
105                 110                 115                 120

TGG ATG AAA TCC ACC AAA GCT CAC GCG TGG AAA AGC AGT GGC AGG A           738
Trp Met Lys Ser Thr Lys Ala His Ala Trp Lys Ser Gln Trp Ala Gly
```

|     |     |     |     |     |     |     |     |     |     | 125 |     |     |     |     | 130 |     |     |     |     | 135 |     |     |     |
|-----|-----|-----|-----|-----|-----|-----|-----|-----|-----|-----|-----|-----|-----|-----|-----|-----|-----|-----|-----|-----|-----|-----|-----|

```
GGT  GCA  TAC  GCA  GCA  GAA  CCG  GAG  GAG  AAT  AAG  AGG  ACC  CGT  ACA  GCC       786
Gly  Ala  Tyr  Ala  Ala  Glu  Pro  Glu  Glu  Asn  Lys  Arg  Thr  Arg  Thr  Ala
              140                      145                      150

TAC  ACT  CGG  GCC  CAG  CTG  CTG  GAG  CTG  GAG  AAG  GAA  TTC  TTA  TTT  AAC       834
Tyr  Thr  Arg  Ala  Gln  Leu  Leu  Glu  Leu  Glu  Lys  Glu  Phe  Leu  Phe  Asn
              155                      160                      165

AAA  TAC  ATC  TCC  CGG  CCT  CGC  CGG  GTG  GAG  CTG  GCA  GTG  ATG  CTC  AAC       882
Lys  Tyr  Ile  Ser  Arg  Pro  Arg  Arg  Val  Glu  Leu  Ala  Val  Met  Leu  Asn
              170                      175                      180

TTG  ACT  GAG  AGA  CAC  ATC  AAA  ATC  TGG  TTC  CAA  AAC  CGT  CGC  ATG  AAG       930
Leu  Thr  Glu  Arg  His  Ile  Lys  Ile  Trp  Phe  Gln  Asn  Arg  Arg  Met  Lys
185                 190                      195                      200

TGG  AAG  AAA  GAG  GAA  GAT  AAG  AAA  CGT  AGT  AGC  GGG  ACA  ACG  AGC  GGG       978
Trp  Lys  Lys  Glu  Glu  Asp  Lys  Lys  Arg  Ser  Ser  Gly  Thr  Thr  Ser  Gly
                        205                      210                      215

GGC  GGT  GGG  GGC  GAA  GAG  CCG  GAG  CAG  GAT  TGT  GCC  GTA  ACC  TCG  GGC      1026
Gly  Gly  Gly  Gly  Glu  Glu  Pro  Glu  Gln  Asp  Cys  Ala  Val  Thr  Ser  Gly
              220                      225                      230

GAG  GAG  CTG  CTG  GCA  TTG  CCA  CCG  CCA  CCA  CCT  CCC  GGA  GGT  GCT  GTG      1074
Glu  Glu  Leu  Leu  Ala  Leu  Pro  Pro  Pro  Pro  Pro  Pro  Gly  Gly  Ala  Val
              235                      240                      245

CCC  TCA  GGC  GTC  CCT  GCT  GCT  GCC  CGG  GAG  GGC  CGA  CTG  CCT  TCC  GGC      1122
Pro  Ser  Gly  Val  Pro  Ala  Ala  Ala  Arg  Glu  Gly  Arg  Leu  Pro  Ser  Gly
     250                      255                      260

CTT  AGT  GCG  TCC  CCA  CAG  CCC  TCC  AGC  ATC  GCG  CCA  CTG  CGA  CCG  CAG      1170
Leu  Ser  Ala  Ser  Pro  Gln  Pro  Ser  Ser  Ile  Ala  Pro  Leu  Arg  Pro  Gln
265                      270                      275                      280

GAA  CCC  CGG  TGAGGACCGC  AGGCTGAGGG  TGAGCGGGTC  TGGGACCCAG                         1219
Glu  Pro  Arg
AGTGCGGACA  TGGGCATGGG  CCCGGGCAGC  TGGATAAGGG  AGGGGATCAT  GAGGCTTAAC                1279

CTAAACGCCA  CACAAGGAGA  ACATTCTTCT  TGGGGGCACA  AGAGCCAGTT  GGGTATAGCC                1339

AGCGAGATGC  TGGCAGACCT  CTGGGAAAAA  AAAAGACCCG  AGCTTCTGAA  AACTTTGAGG                1399

CTGCCTCTCG  TGCCATGTGA  ACCGCCAGGT  CTGCCTCTGG  GACTCTTTCC  TGGGACCAAT                1459

TTAGAGAATC  AGGCTCCCAA  CTGAGGACAA  TGAAAAGGTT  ACAAACTTGA  GCGGTCCCAT                1519

AACAGCCACC  AGGCGAGCTG  GACCGGGTGC  CTTTGACTGG  TCGGCCGAGC  AATCTAAGGT                1579

TGAGAATAAA  GGGAGCTGTT  TGAGGTTTCG  TTTTT                                             1614
```

( 2 ) INFORMATION FOR SEQ ID NO:2:

( i ) SEQUENCE CHARACTERISTICS:
        ( A ) LENGTH: 283 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asn  Ser  Glu  Glu  Gln  Tyr  Tyr  Ala  Ala  Thr  Gln  Leu  Tyr  Lys  Asp
 1                    5                     10                      15

Pro  Cys  Ala  Phe  Gln  Arg  Gly  Pro  Val  Pro  Glu  Phe  Ser  Ala  Asn  Pro
               20                      25                      30

Pro  Ala  Cys  Leu  Tyr  Met  Gly  Arg  Gln  Pro  Pro  Pro  Pro  Pro  Pro  Pro
               35                      40                      45

Gln  Phe  Ala  Gly  Ser  Leu  Gly  Thr  Leu  Glu  Gln  Gly  Ser  Pro  Pro  Asp
          50                      55                      60

Ile  Ser  Pro  Tyr  Glu  Val  Pro  Pro  Leu  Ala  Asp  Asp  Pro  Ala  Gly  Ala
65                       70                      75                      80
```

| His | Leu | His | His | His 85 | Leu | Pro | Ala | Gln | Leu 90 | Gly | Leu | Ala | His | Pro 95 | Pro |
|---|---|---|---|---|---|---|---|---|---|---|---|---|---|---|---|
| Pro | Gly | Pro | Phe 100 | Pro | Asn | Gly | Thr | Glu 105 | Thr | Gly | Gly | Leu | Glu 110 | Glu | Pro |
| Ser | Arg | Val 115 | His | Leu | Pro | Phe | Pro 120 | Trp | Met | Lys | Ser | Thr 125 | Lys | Ala | His |
| Ala | Trp 130 | Lys | Ser | Gln | Trp | Ala 135 | Gly | Gly | Ala | Tyr | Ala 140 | Ala | Glu | Pro | Glu |
| Glu 145 | Asn | Lys | Arg | Thr | Arg 150 | Thr | Ala | Tyr | Thr | Arg 155 | Ala | Gln | Leu | Leu | Glu 160 |
| Leu | Glu | Lys | Glu | Phe 165 | Leu | Phe | Asn | Lys | Tyr 170 | Ile | Ser | Arg | Pro | Arg 175 | Arg |
| Val | Glu | Leu | Ala 180 | Val | Met | Leu | Asn | Leu 185 | Thr | Glu | Arg | His | Ile 190 | Lys | Ile |
| Trp | Phe | Gln 195 | Asn | Arg | Arg | Met | Lys 200 | Trp | Lys | Lys | Glu | Glu 205 | Asp | Lys | Lys |
| Arg | Ser 210 | Ser | Gly | Thr | Thr | Ser 215 | Gly | Gly | Gly | Gly | Gly 220 | Glu | Glu | Pro | Glu |
| Gln 225 | Asp | Cys | Ala | Val | Thr 230 | Ser | Gly | Glu | Glu | Leu 235 | Leu | Ala | Leu | Pro | Pro 240 |
| Pro | Pro | Pro | Pro | Gly 245 | Gly | Ala | Val | Pro | Ser 250 | Gly | Val | Pro | Ala | Ala 255 | Ala |
| Arg | Glu | Gly | Arg 260 | Leu | Pro | Ser | Gly | Leu 265 | Ser | Ala | Ser | Pro | Gln 270 | Pro | Ser |
| Ser | Ile | Ala 275 | Pro | Leu | Arg | Pro | Gln 280 | Glu | Pro | Arg | | | | | |

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: promoter
        ( B ) LOCATION: 1..19
        ( D ) OTHER INFORMATION: /function="Somatostatin TSE-I
            region"

( x i ) SEQUENCE DESCRIPTION: SEQ ID NO:3:

TTGCGAGGCT AATGGTGCG                                                19

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: promoter
        ( B ) LOCATION: 1..22
        ( D ) OTHER INFORMATION: /function="Somatostatin TSE-II
            region"

( x i ) SEQUENCE DESCRIPTION: SEQ ID NO:4:

GATCTCAGTA ATAATCATGC AG                                                  22

(2) INFORMATION FOR SEQ ID NO:5:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: Other nucleic acid;
       (A) DESCRIPTION: Oligonucleotide (xi) SEQUENCE DESCRIPTION: SEQ ID NO:5:

GGCGGATCCC TNRARARRGA RTWC                                                24

(2) INFORMATION FOR SEQ ID NO:6:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: Other nucleic acid;
       (A) DESCRIPTION: Oligonucleotide (xi) SEQUENCE DESCRIPTION: SEQ ID NO:6:

GGCGGATCCC KRTTYTGRAA CCA                                                 23

(2) INFORMATION FOR SEQ ID NO:7:

(i) SEQUENCE CHARACTERISTICS:
       (A) LENGTH: 23 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:7:

GATCTCAGGC CGGCCGCATG CAC                                                 23

(2) INFORMATION FOR SEQ ID NO:8:

(i) SEQUENCE CHARACTERISTICS:
       (A) LENGTH: 19 base pairs
       (B) TYPE: nucleic acid
       (C) STRANDEDNESS: double
       (D) TOPOLOGY: linear (ii) MOLECULE TYPE: DNA (genomic)

(ix) FEATURE:
       (A) NAME/KEY: promoter
       (B) LOCATION: 1..19
       (D) OTHER INFORMATION: /function="Rat Insulin-I "P-Box"
               region"

(xi) SEQUENCE DESCRIPTION: SEQ ID NO:8:

CTTAATGGGC CAAACGGCA                                                      19

(2) INFORMATION FOR SEQ ID NO:9:

(i) SEQUENCE CHARACTERISTICS:
       (A) LENGTH: 18 base pairs
       (B) TYPE: nucleic acid
       (C) STRANDEDNESS: double
       (D) TOPOLOGY: linear (ii) MOLECULE TYPE: DNA (genomic)

(ix) FEATURE:
  (A) NAME/KEY: promoter
  (B) LOCATION: 1..18
  (D) OTHER INFORMATION: /function="Rat Insulin-I "E2" region"

(xi) SEQUENCE DESCRIPTION: SEQ ID NO:9:

TTAATAATCT AATTACCC                18